US005888611A

United States Patent [19]

Leonard

[11] Patent Number: 5,888,611

[45] Date of Patent: Mar. 30, 1999

[54] MULTILAYER HOLLOW FIBER BODY AND METHOD OF MAKING

[76] Inventor: Ronald J. Leonard, P.O. Box 33427, St. Paul, Minn. 55133-3427

[21] Appl. No.: 70,711

[22] Filed: Apr. 30, 1998

Related U.S. Application Data

[63] Continuation of Ser. No. 822,523, Apr. 16, 1997, Pat. No. 5,747,138, which is a continuation of Ser. No. 565,439, Nov. 30, 1995, abandoned.

[51] Int. Cl.[6] .......... B32B 5/12

[52] U.S. Cl. .......... 428/113; 428/124; 428/126; 493/405

[58] Field of Search .......... 428/113, 124, 428/126; 493/405

[56] References Cited

U.S. PATENT DOCUMENTS

| | | | |
|---|---|---|---|
| 2,217,370 | 10/1940 | Johnston | 166/7 |
| 3,198,335 | 8/1965 | Lewis et al. | 210/321 |
| 3,211,148 | 10/1965 | Galajda, Jr. | 128/214 |
| 3,339,341 | 9/1967 | Maxwell et al. | 55/16 |
| 3,412,865 | 11/1968 | Lontz et al. | 210/321 |
| 3,422,008 | 1/1969 | McLain | 210/22 |
| 3,468,631 | 9/1969 | Raible et al. | 23/258.5 |
| 3,489,647 | 1/1970 | Kolobow | 195/1.8 |
| 3,536,611 | 10/1970 | Filippi et al. | 210/22 |
| 3,557,962 | 1/1971 | Kohl | 210/321 |
| 3,615,238 | 10/1971 | Bentley et al. | 23/258.5 |
| 3,690,465 | 9/1972 | McGinnis et al. | 210/321 |
| 3,794,468 | 2/1974 | Leonard | 23/258.5 |
| 3,927,980 | 12/1975 | Leonard | 23/258.5 |
| 3,989,626 | 11/1976 | Bentley et al. | 210/177 |
| 4,022,692 | 5/1977 | Janneck | 210/321 |
| 4,045,851 | 9/1977 | Ashare et al. | 29/157 |
| 4,140,637 | 2/1979 | Walter | 210/321 |
| 4,172,794 | 10/1979 | Sigdell | 210/232 |
| 4,188,360 | 2/1980 | Kurata | 422/46 |
| 4,213,858 | 7/1980 | Boberg et al. | 210/23 |
| 4,224,094 | 9/1980 | Amicel et al. | 156/169 |

(List continued on next page.)

FOREIGN PATENT DOCUMENTS

| | | |
|---|---|---|
| 0 041 467 | 12/1981 | European Pat. Off. . |
| 0 093 677 | 11/1983 | European Pat. Off. . |
| 0 345 983 | 12/1989 | European Pat. Off. . |
| 0 515 033 | 11/1992 | European Pat. Off. . |
| 0 285 812 | 10/1993 | European Pat. Off. . |
| 0 621 047 | 10/1994 | European Pat. Off. . |

(List continued on next page.)

OTHER PUBLICATIONS

Brochure “Choisissez La Securite . . . Oxygenateurs—Oxpal—M4”; Hospal France.

Brochure “Description of the M 3 Oxygenators” Hospal, Paris; 1979 (some translation).

Brochure “Rhone–Poulenc Genie Medical—L’oxygenateur a Membrane M 3”; Medical Department Genie Medical, Paris; 74 B 6333.

Brochure “Travenol—code 5M1431—LPM/50 Membrane Oxygenator—Low Pressure Adult Oxygenator with Integral Heat Exchanger and Reservoir—Directions for Use”; Travenol Laboratories Inc.; Jan. 1982.

(List continued on next page.)

*Primary Examiner*—Christopher Raimund
*Attorney, Agent, or Firm*—Gary L. Griswold; Robert W. Sprague; Stephen W. Bauer

[57] ABSTRACT

A multilayer hollow fiber body useful, for example, in a blood oxygenator. The multilayer hollow fiber body comprises a single hollow fiber mat arranged in the form of a body comprising a plurality of hollow fiber plies. The mat comprises a plurality of generally parallel hollow fibers disposed at regular intervals, and a plurality of connecting fibers holding the connecting fibers. The mat is repeatedly folded over on itself along fold lines, each of which is at an oblique angle to the hollow fibers, to form a multilayer hollow fiber body in which the hollow fibers of any ply of the multilayer hollow fiber body are disposed so as to cross the hollow fibers of an adjacent successive ply of the multilayer hollow fiber body. Also disclosed is a method of making the multilayer hollow fiber body.

13 Claims, 8 Drawing Sheets

FL-2
22
24
FL-1
22
20
σ

U.S. PATENT DOCUMENTS

| | | | |
|---|---|---|---|
| 4,227,295 | 10/1980 | Bodnar et al. | 29/527.3 |
| 4,256,692 | 3/1981 | Cover | 422/46 |
| 4,301,013 | 11/1981 | Setti et al. | 210/637 |
| 4,315,819 | 2/1982 | King et al. | 210/321.3 |
| 4,343,668 | 8/1982 | Francisoud et al. | 156/172 |
| 4,346,006 | 8/1982 | Kopp et al. | 210/321.4 |
| 4,350,549 | 9/1982 | Frehner | 156/161 |
| 4,424,190 | 1/1984 | Mather, III et al. | 422/46 |
| 4,430,219 | 2/1984 | Kuzumoto et al. | 210/321.3 |
| 4,440,641 | 4/1984 | Ostertag | 210/321.3 |
| 4,451,562 | 5/1984 | Elgas et al. | 435/2 |
| 4,469,659 | 9/1984 | Carson et al. | 422/46 |
| 4,533,089 | 8/1985 | Sartor et al. | 242/7.21 |
| 4,559,884 | 12/1985 | Stoldt et al. | 112/262.1 |
| 4,559,999 | 12/1985 | Servas et al. | 165/156 |
| 4,572,446 | 2/1986 | Leonard et al. | 242/7.02 |
| 4,639,353 | 1/1987 | Takemura et al. | 422/46 |
| 4,659,549 | 4/1987 | Hamada et al. | 422/48 |
| 4,689,255 | 8/1987 | Smoot et al. | 428/77 |
| 4,690,758 | 9/1987 | Leonard et al. | 210/247 |
| 4,715,953 | 12/1987 | Leonard | 210/321.8 |
| 4,735,775 | 4/1988 | Leonard et al. | 422/46 |
| 4,770,852 | 9/1988 | Takahara et al. | 422/48 |
| 4,791,054 | 12/1988 | Hamada et al. | 435/2 |
| 4,818,490 | 4/1989 | Carson et al. | 422/46 |
| 4,902,416 | 2/1990 | Schroeder et al. | 210/321.67 |
| 4,906,372 | 3/1990 | Hopkins | 210/321.74 |
| 4,911,846 | 3/1990 | Akasu et al. | 210/645 |
| 4,940,617 | 7/1990 | Baurmeister | 428/36.3 |
| 4,952,312 | 8/1990 | Zantonelli et al. | 210/321.74 |
| 4,971,836 | 11/1990 | Fukasawa et al. | 427/235 |
| 4,975,247 | 12/1990 | Badolato et al. | 422/48 |
| 5,015,379 | 5/1991 | Drori | 210/411 |
| 5,026,479 | 6/1991 | Bikson et al. | 210/321.8 |
| 5,039,482 | 8/1991 | Panzani et al. | 422/46 |
| 5,043,140 | 8/1991 | Combs | 422/46 |
| 5,102,533 | 4/1992 | Oshiyama | 210/85 |
| 5,120,501 | 6/1992 | Mathewson et al. | 422/46 |
| 5,139,529 | 8/1992 | Seita et al. | 623/66 |
| 5,139,741 | 8/1992 | Hagiwara | 422/48 |
| 5,143,312 | 9/1992 | Baurmeister | 242/7.02 |
| 5,160,672 | 11/1992 | Sasaki et al. | 264/41 |
| 5,186,835 | 2/1993 | Masuoka et al. | 210/500.36 |
| 5,188,801 | 2/1993 | Fini | 422/48 |
| 5,192,499 | 3/1993 | Sakai et al. | 422/46 |
| 5,202,025 | 4/1993 | Onishi et al. | 210/500.35 |
| 5,225,161 | 7/1993 | Mathewson et al. | 422/46 |
| 5,236,665 | 8/1993 | Mathewson et al. | 422/46 |
| 5,240,677 | 8/1993 | Jones et al. | 422/46 |
| 5,255,734 | 10/1993 | Leonard et al. | 165/96 |
| 5,266,265 | 11/1993 | Raible | 422/46 |
| 5,270,004 | 12/1993 | Cosentino et al. | 422/46 |
| 5,270,005 | 12/1993 | Raible | 422/46 |
| 5,279,738 | 1/1994 | Seita et al. | 210/500.38 |
| 5,284,584 | 2/1994 | Huang et al. | 210/321.61 |
| 5,294,401 | 3/1994 | Hagiwara | 422/48 |
| 5,312,589 | 5/1994 | Reeder et al. | 422/45 |
| 5,338,512 | 8/1994 | Mathewson et al. | 422/46 |
| 5,346,621 | 9/1994 | Haworth et al. | 210/645 |
| 5,376,334 | 12/1994 | Haworth et al. | 422/46 |
| 5,421,405 | 6/1995 | Goodin et al. | 165/154 |
| 5,449,457 | 9/1995 | Prasad | 210/321.8 |
| 5,462,619 | 10/1995 | Haworth et al. | 156/172 |
| 5,489,382 | 2/1996 | Tatebe et al. | 210/321.89 |
| 5,514,335 | 5/1996 | Leonard et al. | 442/46 |
| 5,580,522 | 12/1996 | Leonard et al. | 422/46 |
| 5,733,398 | 3/1998 | Carson et al. | 156/69 |
| 5,747,138 | 5/1998 | Leonard | 428/113 |
| 5,762,868 | 6/1998 | Leonard | 422/46 |

FOREIGN PATENT DOCUMENTS

| | | |
|---|---|---|
| 2 222 134 | 10/1974 | France . |
| 2 351 041 | 12/1977 | France . |
| 23 00 312 | 7/1973 | Germany . |
| 24 41 333 | 3/1975 | Germany . |
| 27 21 444 | 11/1978 | Germany . |
| 79 11 220 | 4/1979 | Germany . |
| 28 25 065 | 12/1979 | Germany . |
| 28 39 937 | 4/1980 | Germany . |
| 32 36 946 | 4/1984 | Germany . |
| 207 607 | 7/1984 | Germany . |
| 233 946 | 3/1986 | Germany . |
| 36 34 307 | 1/1988 | Germany . |
| 37 33 542 | 7/1988 | Germany . |
| 38 39 567 | 6/1990 | Germany . |
| 49-55569 | 5/1974 | Japan . |
| 52-38836 | 10/1977 | Japan . |
| 53-39695 | 4/1978 | Japan . |
| 54-136579 | 10/1979 | Japan . |
| 56-78601 | 6/1981 | Japan . |
| 57-53205 | 3/1982 | Japan . |
| 58-155862 | 9/1983 | Japan . |
| 59-11866 | 1/1984 | Japan . |
| 62-57965 | 3/1987 | Japan . |
| 62-72364 | 4/1987 | Japan . |
| 1040060 | 2/1989 | Japan . |
| 1-176405 | 7/1989 | Japan . |
| 2-109572 | 4/1990 | Japan . |
| 2-172522 | 7/1990 | Japan . |
| 4-2066 | 1/1992 | Japan . |
| 6-31143 | 2/1994 | Japan . |
| 6-114243 | 4/1994 | Japan . |
| 1075066 | 7/1967 | United Kingdom . |
| 1481064 | 7/1977 | United Kingdom . |
| WO 83/00098 | 1/1983 | WIPO . |
| WO 90/04419 | 5/1990 | WIPO . |
| WO 90/07943 | 7/1990 | WIPO . |
| WO 95/11709 | 5/1995 | WIPO . |

OTHER PUBLICATIONS

Brochure “The new alternative to bubble oxygenators from TRAVENOL”; Travenol Laboratories Inc., Cardiopulmonary Products; 1982.

Brochure “TMO Oxygenator Integrated Circuit System—passes the test of time”; Cardiopulmonary Products, Travenol Laboratories, Inc.; 1982.

Brochure “Travenol TMO membrane oxygenator—Improved for consistent performance . . . ”; Travenol Laboratories, Inc., Artificial Organs Division Jan. 1979.

Brochure “the Travenol membrane oxygenator”; Artificial Organs Division of Travenol Laboratories, Inc. Jan. 1977.

Flyer “SMO/ICR Sarns Membrane Oxygenator with Integral Cardiotomy Reservoir”; 3M 1990; Form No. 78–8066–9349–1.

Mockros et al.; “Compact Cross–Flow Tubular Oxygenators”; vol. XXXI, Trans. Am Soc. Artif Intern Organs 1985.

“Processes and Units for Reverse Osmosis and Ion Exchange”; Hollow Fibers–Manufacture and Applications; Chemical Technology Review No. 194; 1981.

Brochure “Sarns® SMO/INF Infant Membrane Oxygenator–Instructions”; 3M; Dec., 1989; Form No. 16499401 R/D.

Brochure “Sarns™ SMO/IR Membrane Oxygenator with Integral Reservoir–Instructions”; 3M; Mar. 1990; Form No. 34–9998–9113–7 R/A.

Flyer “SMO/IR Sarns Membrane Oxygenator with Integral Reservoir”; 3M, 1990; Form No. 78–8066–9350–9.

Flyer “SMO/INF Sarns Infant Membrane Oxygenator”; 3M, 1990; Form No. 78–8066–9351–7.

Brochure “When you bring efficiency of the surface . . . you can lower the prime.”; 3M; 1990; Form No. 16088004 Rev. B.

30D

32D

MULTILAYER HOLLOW FIBER BODY AND METHOD OF MAKING

RELATED APPLICATIONS

This is a continuation of Ser. No. 08/822,523, filed Apr. 16, 1997, now U.S. Pat. No. 5,747,138, which is a continuation of Ser. No. 08/565,439, filed Nov. 30, 1995, now abandoned.

FIELD OF THE INVENTION

This invention relates to a multilayer hollow fiber body and method of making such a body, and more particularly to such a hollow fiber body that is useful in blood oxygenators and other medical equipment.

BACKGROUND OF THE INVENTION

In the field of membrane blood oxygenators employing a multiplicity of porous hollow fibers, it has long been recognized that gas transfer between the lumens of the hollow fibers and the blood circulating outside the fibers is optimized when the fibers of adjacent layers cross one another. For example, U.S. Pat. No. 3,794,468 (Leonard) discloses winding a single porous hollow fiber around a core in such a way that the hollow fiber along one layer is generally parallel to itself but disposed at an angle to the hollow fiber of the immediately adjacent layers. This provides flow channels for fluid on the outside of the hollow fibers having low resistance and desirable flow characteristics without the use of spacers between the layers, which would undesirably increase the prime volume of the resulting product and surface area that blood contacts.

U.S. Pat. Nos. 4,940,617 and 5,143,312 (Baurmeister '617 and '312) disclose forming a structure comprising two superimposed hollow fiber mats that are then spirally wound to form a multilayer hollow fiber body. Each mat comprises a plurality of generally parallel hollow fibers that are held by solid transverse fibers. The hollow fibers of the two superimposed mats are disposed at an equal but opposite angle (other than perpendicular) to the longitudinal direction of the mat. The result is that the hollow fibers of adjacent layers cross one another to form flow channels without the use of spacers. While the concept of employing a mat has certain manufacturing advantages, one problem with the Baurmeister method and product is that it requires the use of two fiber mats in order to accomplish the result of crossing the hollow fibers of adjacent layers. The mats disclosed in the Baurmeister patents are available from Akzo Nobel Faser AG, Wuppertal, Germany.

An additional restriction or limitation of the prior systems discussed above is that they require the hollow fiber structure to extend completely around a core or otherwise form an unbroken wound structure.

SUMMARY OF THE INVENTION

This invention provides a multilayer hollow fiber body and a method of making such a body with a single hollow fiber mat, rather than two superimposed hollow fiber mats or a structure wound from a single fiber, in which the hollow fibers of adjacent plies or layers of the body cross one another at a desired angle. The resulting hollow fiber body may be formed in many different configurations and used in many different products, particularly including an integral blood oxygenator, heat exchanger and filter, in which the hollow fiber body is wrapped around a heat exchanger manifold, with a gap being formed between edges of the hollow fiber body to receive a blood filter. The hollow fiber body may also be kept in a generally flat configuration, or wrapped completely around a core with opposite edges of the body engaging one another. The different configurations that the hollow fiber body may take relative to the prior systems discussed in the background reduces limitations and restrictions on the design of products employing such hollow fiber bodies, such as blood oxygenators, blood heat exchangers, dialyzers and other products, in comparison to those prior systems. The hollow fiber body is designed to promote mixing of blood flow around the hollow fibers without excessive pressure drop.

Generally, a multilayer hollow fiber body of the invention comprises a single hollow fiber mat arranged in the form of a body comprising a plurality of hollow fiber plies. The mat comprises a plurality of hollow fibers disposed at regular intervals and a plurality of connecting fibers holding the hollow fibers. The mat is repeatedly folded over on itself along fold lines, each of which is at an oblique angle to the hollow fibers, to form a multilayer hollow fiber body in which the hollow fibers of any ply of the multilayer hollow fiber body are disposed so as to cross the hollow fibers of an adjacent successive ply of the multilayer hollow fiber body.

Preferably, the fold lines are generally parallel to one another, and the oblique angle between the hollow fibers and the fold lines is between approximately 1–15 degrees. Most preferably, the mat is generally elongate, the hollow fibers extend at an oblique angle (e.g., 75–89 degrees) with respect to the direction of elongation of the mat, and the fold lines are generally perpendicular to the direction of elongation of the mat.

Also, preferably, the connecting fibers are disposed at regular intervals, extend generally in the direction of elongation of the mat, and are interweaved with the hollow fibers to hold the fibers in the mat.

Most preferably, the distance between the fold lines along any ply is the same as the distance between the fold lines along any other ply. Alternatively, the distance between the fold lines along any ply may progressively increase in an "outer" direction.

In the method of the invention, a multilayer hollow fiber body is made according to the following steps:

(A) interweaving hollow fibers and connecting fibers to form a mat, with the hollow fibers being generally parallel to one another; and (B) repeatedly folding the mat over on itself along fold lines that are at an oblique angle to the hollow fibers to form a multilayer hollow fiber body in which the hollow fibers of any ply of the multilayer hollow fiber body are disposed so as to cross the follow fibers of an adjacent successive ply of the multilayer hollow fiber body.

The mat is preferably folded along generally parallel fold lines that are generally perpendicular to the direction of elongation of the mat, and equally spaced apart so that any ply of the mat has a length between fold lines that is generally equal to the length of the other plies Other features will be pointed out hereinafter.

BRIEF DESCRIPTION OF THE DRAWING

The invention will be further described with reference to the drawing wherein corresponding reference characters indicate corresponding parts throughout the several views of the drawing, and wherein.

DETAILED DESCRIPTION OF PREFERRED EMBODIMENTS

Figure 1:
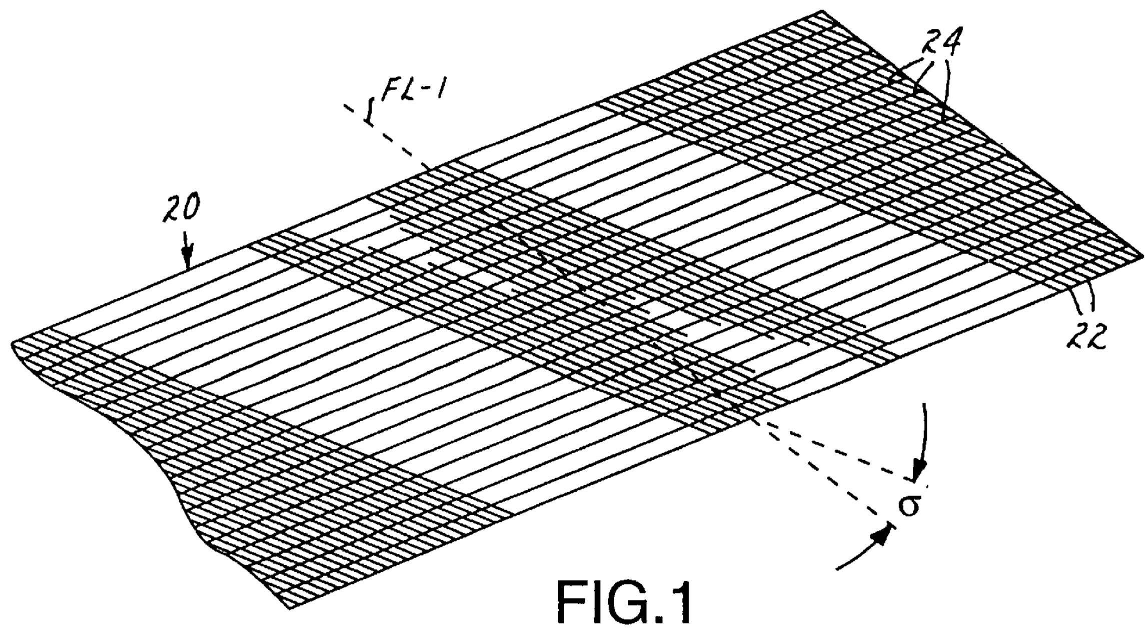
FIG. 1 is perspective view of an elongate, continuous mat of hollow fiber material, illustrating a preferred oblique angle of the hollow fibers relative to the longitudinal axis of the mat.

Now referring to the drawing, an elongate, generally continuous mat of the invention is designated by the reference numeral 20. The mats 20 may be of the type conventionally used in blood oxygenators, and are available under the trade designation "OXYPHAN™" membranes from the Fibers Division of Akzo Nobel Faser AG, Wuppertal, Germany, or under the trade designation "CELGARD™ hollow fiber array" from the Separations Products Division of Hoechst Celanese Corporation, Charlotte, N.C. These mats 20 are conventionally formed of polypropylene.

The mat 20 includes a multiplicity of conventional microporous hollow fibers 22, and conventional connecting fibers 24 (FIG. 7D) holding the hollow fibers 22. The hollow fibers 22 and connecting fibers 24 are preferably interweaved so that the connecting fibers 24 hold the hollow fibers 22 in an array. The connecting fibers 24 are preferably solid, rather than hollow. Each hollow fiber 22 comprises a lumen 26 and a wall 28 defining the lumen 26. The wall 28 is generally microporous to allow transfer of gas but not liquid through the wall 28 so that oxygen may pass outwardly from the lumen 26 through the wall 28 into blood circulating outside the hollow fiber 22 and so that carbon dioxide may pass inwardly from the blood through the wall 28 into the lumen 26 so that it may be carried away. According to one example of the invention, approximately thirty hollow fibers 22 are provided per inch (12 fibers per centimeter), and each hollow fiber 22 has an outer diameter of approximately 300 micrometers.

The hollow fibers 22 are disposed at regular intervals, and the connecting fibers 24 are preferably disposed at regular intervals. As used herein, the term "regular intervals" does not require equal intervals, although equal intervals are preferred. Rather, the term "regular intervals" means, for example, that the hollow fibers 22 are generally parallel to one another in the mat 20 before the mat 20 is folded. As will be discussed below, after the mat 20 is folded, the hollow fibers 22 of one ply will be parallel to one another but will cross the hollow fibers 22 of adjacent plies.

As used herein, the terms "longitudinal", "longitudinally" or "direction of elongation of the mat" refer to the elongate or continuous direction of the mat 20, and the terms "lateral" or "laterally" refer to the direction across the width of the mat 20, which is perpendicular to the longitudinal direction of the mat 20. The term "length" in connection with the mat 20 refers to a distance in the longitudinal direction of the mat 20. The term "width" of the mat 20 refers to the distance laterally across the mat 20. As used herein, the terms "elongate" or "direction of elongation" do not imply or require the mat to be stretched; they simply refer to the longer dimension of the mat.

The connecting fibers 24 extend generally in the longitudinal direction of the mat 20, and the hollow fibers 22 extend at an oblique angle σ relative to the lateral direction of the mat. As used herein, the term "oblique angle" refers to an angle other than zero, 90, 180, 270 or 360 degrees. The oblique angle σ is preferably 1–15 degrees (e.g., 5 degrees). The hollow fibers 22 can also be considered as extending at an oblique angle relative to the longitudinal direction of the mat 20, which is equal to ninety minus the oblique angle σ. Thus, the hollow fibers 22 preferably extend at an oblique angle of approximately 75–89 degrees (e.g., 85 degrees) relative to the longitudinal direction of the mat 20. The oblique angle can be formed in the original production of the mat 20, or by flexing or displacing one edge of the mat 20 longitudinally relative to the opposite edge of the mat 20.

Most preferably, the mat 20 is provided in roll-form with the hollow fibers 22 pre-skewed at the desired oblique angle. Alternatively, the mat 20 could be provided with the hollow fibers 22 arranged generally perpendicularly to the longitudinal direction of the mat 20, and the first ply of the mat 20 could be held in a folding apparatus with the hollow fibers 22 skewed at the desired oblique angle, or the mat 20 could be processed between the mat-supply roll and the folding apparatus to orient the hollow fibers 22 at the desired oblique angle.

Figure 2:
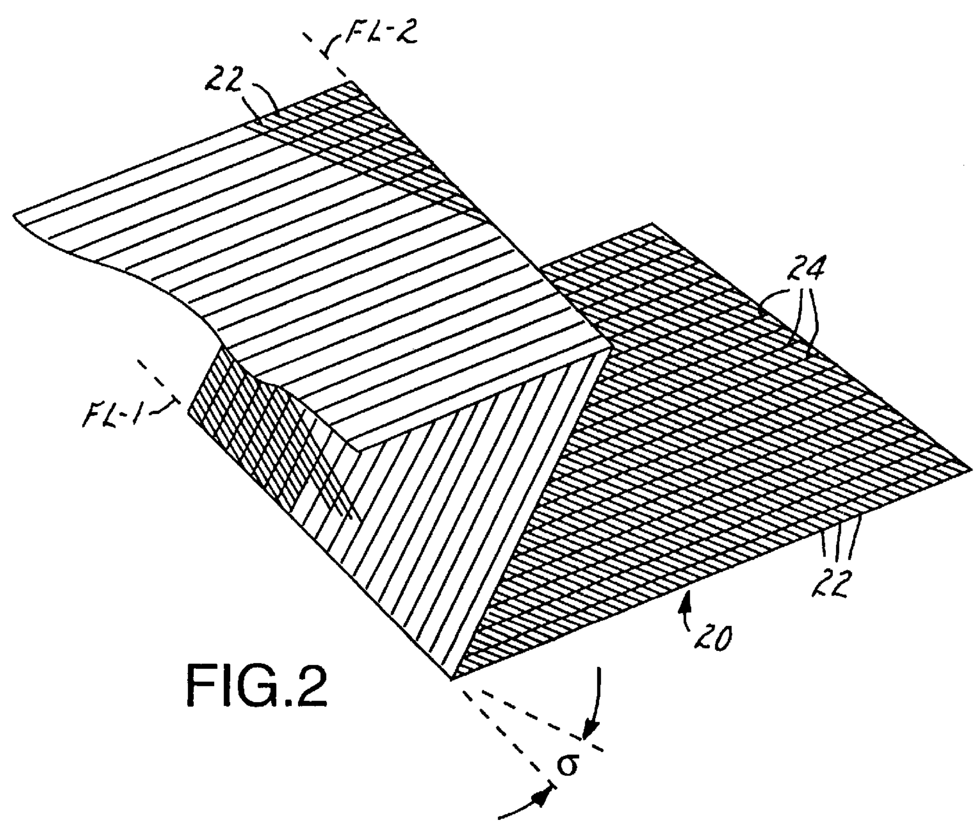
FIG. 2 is a perspective view of the mat of FIG. 1 being folded along fold lines that are substantially perpendicular to the longitudinal axis of the mat.
Figures 3, 4, 5, 6:
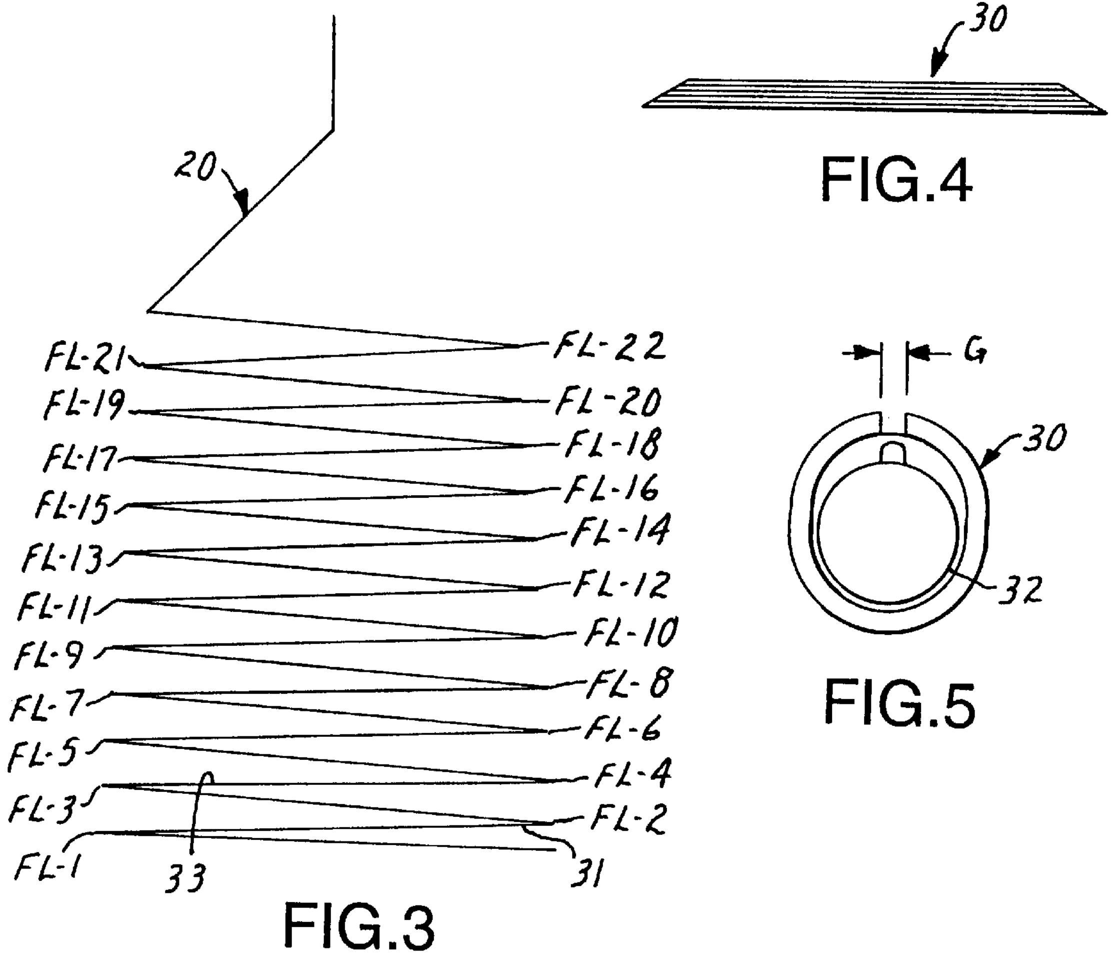
FIG. 3 is side view of the mat of FIGS. 1 and 2 being folded along fold lines resulting in successive layers have successively decreasing length.
FIG. 4 is a side view of a multilayer hollow fiber body formed by the mat folded as illustrated in FIG. 3.
FIG. 5 is an end view of some of the interior components of a novel blood oxygenator and heat exchanger, including the multilayer hollow fiber body of FIG. 4 formed into a generally "C" shaped body.
FIG. 6 is a side view of a multilayer hollow fiber body formed into a generally "C" shaped body where each successive layer of the mat has the same length as the other layers.

As illustrated in FIGS. 2 and 3, the mat 20 is repeatedly folded over on itself along fold lines, e.g., FL-1, FL-2, . . ., FL-22, FL-N, that are disposed at an oblique angle relative to the hollow fibers 22. "N", for example, could equal approximately 50 fold lines. The repeatedly folded mat 20 forms a multilayer hollow fiber body 30 in which the hollow fibers 22 of any ply, e.g., 31, of the body 30 are disposed so as to cross the hollow fibers 22 of an adjacent successive ply, e.g., 33, of the body 30. Preferably, the fold lines FL-1, FL-2 are generally parallel to one another, and extend generally laterally across the mat 20 so that they are at the oblique angle σ relative to the hollow fibers 22. The result is that the hollow fibers 22 of one ply cross over the previous ply at an oblique angle 2σ. Opposite edges 34 and 36 of the body 30 are defined by the fold lines FL-1, FL-2, . . ., FL-N, of the mat 20. Most preferably, the mat 20 is not crimped along the fold lines, FL-1, FL-2, . . ., FL-N, so that gas may flow through any hollow fibers 22 that extend past the fold lines.

Figure 7A:
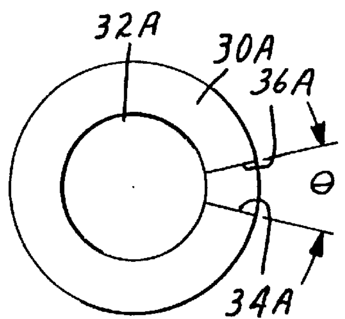
FIG. 7A is a side schematic view of a generally "C" shaped multilayer hollow fiber body formed over a cylinder, illustrating an angle θ formed between the edges of the multilayer hollow fiber body of FIG. 6.
Figure 7B:
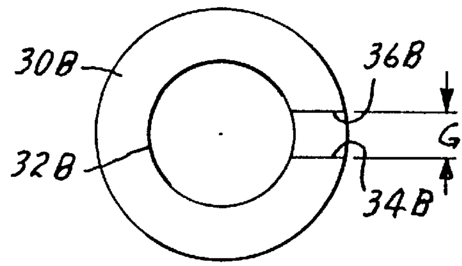
FIG. 7B is a side schematic view of a generally "C" shaped multilayer hollow fiber body formed over a cylinder, illustrating a generally constant gap "G" between the edges of a multilayer hollow fiber body folded as illustrated in FIGS. 3–5.
Figure 7C:
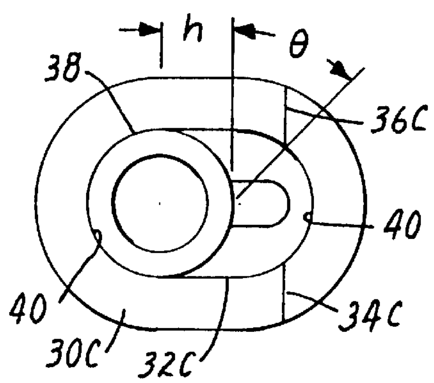
FIG. 7C is a side schematic view of a generally "C" shaped multilayer hollow fiber body formed over a core having an oblong cross section, illustrating a dimension "H" and an angle θ used in calculating the desired width of each successive layer of the mat.

FIGS. 3 and 4 illustrate one preferred embodiment of the invention, in which the plies are laid down in successively decreasing lengths, forming a trapezoid-like shape when viewed from the side. When the resulting body 30 of this embodiment is wrapped around a manifold 32, the ends 34 and 36 of the body 30 may be separated by a constant width gap "G", as illustrated in FIG. 5. FIGS. 7A, 7B and 7C illustrate various geometrical aspects to control the configuration of the gap, which are used to specify the length of each of the plies that form the mat.

FIG. 7A illustrates geometrical aspects of designing the multilayer hollow fiber body, here 30A, to have a gap that increases by a constant angle θ concentric with the axis of a generally cylindrical manifold 32A around which the body 30A is wrapped. The body 30A may be considered as having an arcuate or generally C-shaped configuration when viewed from the side as in FIG. 7A. The distance along any ply between the fold lines defining that ply may be determined by the following equation:

$$Ln=Ln=\pi(D+2(n-1)d+d)(1-\theta/360)$$

Figure 7D:
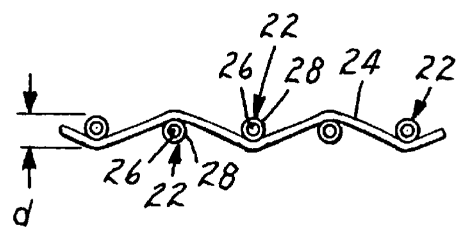
FIG. 7D is an enlarged side view of a small section of the mat of FIGS. 1–7C, illustrating the outer diameter "d" of a hollow fiber and a lumen of the hollow fiber and the weaving of a connecting fiber between the hollow fibers.

Where:

n=Number of ply starting with 1 at inner ply;

Ln=Distance between fold lines of ply n;

D=Outer diameter of manifold;

d=Outer diameter of hollow fiber illustrated in FIG. 7D; and

θ=Gap angle θ illustrated in FIG. 7A.

FIG. 7B illustrates geometrical aspects of designing the multilayer hollow fiber body, here 30B, to have a constant width or uniform gap G when wrapped around a generally cylindrical manifold 32B. The opposite edges 34B, 36B of the body 30B of this embodiment either engage one another or are separated by a constant width gap G. The distance Ln along a ply between fold lines is substantially determined by the following equation:

$$Ln=\pi(D+2(n-1)d+d)-G$$

Where:

n=Number of ply starting with 1 at inner ply;

Ln=Distance between fold lines of ply n;

D=Outer diameter of manifold;

d=Outer diameter of hollow fiber; and

G=Desired uniform gap between the opposite edges of the mat, which may be zero if the opposite edges engage one another.

FIG. 7C illustrates geometrical aspects of designing a multilayer hollow fiber body, here 30C, wrapped around a manifold 32C having a generally oblong cross-sectional configuration in such a manner that the opposite edges 34C and 36C of the body 30C define a gap with edges perpendicular to the linear edges 38 of the cross section adjoining the semi-circles 40. The body 30C may be considered as having a generally arcuate "U" shape when viewed from the side as in FIG. 7C. The distance Ln along a ply between fold lines is substantially determined by the following equation:

$$Ln=\frac{\pi}{2}(D+2(n-1)d+d)+2h+\pi D(2\theta/360)$$

Where:

n=Number of ply starting with 1 at inner ply;

Ln=Distance between fold lines of ply n;

D=Outer diameter of semi-circles of manifold;

d=Outer diameter of hollow fiber;

h=Distance between semi-circles along linear edge; and

θ=Angle forming the arc of ply length at one edge centered on the semicircle with the gap.

According to the most preferred embodiment of the invention, however, the distance between the fold lines FL-1, FL-2, etc., along any ply is the same as the distance between the fold lines along any other ply. As illustrated in FIG. 6, when the multilayer hollow fiber body, here 30D, is wrapped over an oblong manifold 32D, the "inner" plies extend farther around the manifold 32D than do the "outer" plies. This is also true if the manifold is generally cylindrical as well as other configurations. As used herein, the term "inner ply" refers to the ply closest to the manifold 32A, and the term "outer ply" refers to the ply farthest from the manifold 32A. This feature provides certain advantages when employed in the integral blood oxygenator, heat exchanger and filter described in a co-assigned U.S. patent application filed on the same day as this application by Ronald J. Leonard, Attorney Docket No. 50999 USA 9A, Express Mail Label No. EH086388681US, dated Nov. 30, 1995, titled "Blood Oxygenator and Heat Exchanger", which is hereby incorporated herein by reference. For example, since the outer plies do not extend as far around the unit as do the inner plies, they open up a space between the hollow fiber body and the blood filter that can facilitate venting of gas upstream of the blood filter or use of a bypass port to bypass the filter.

Figure 19:
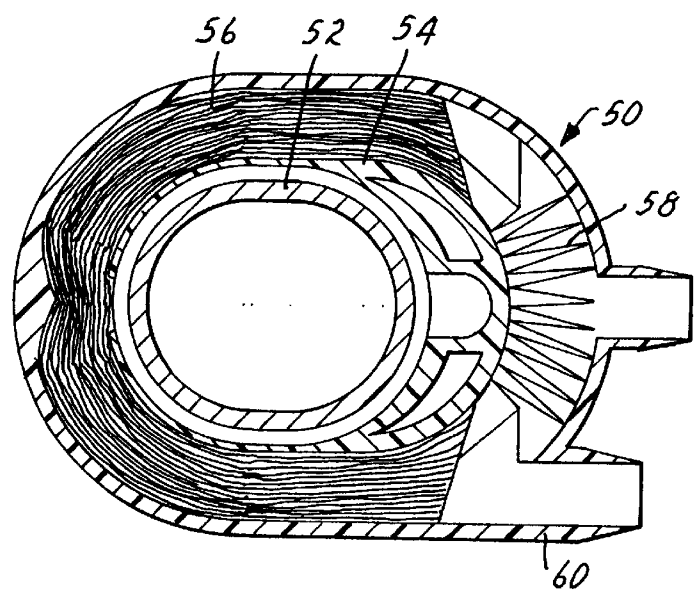
FIG. 19 is a cross sectional view of an integral blood oxygenator, heat exchanger and filter incorporating a multilayer hollow fiber body of the invention.

FIG. 19 is a cross sectional view illustrating various features of one of the embodiments of the integral blood oxygenator, heat exchanger and filter described in more detail in the co-assigned patent application. That apparatus 50 generally comprises a generally cylindrical stainless steel heat exchanger barrier 52, generally oblong flexible plastic inlet manifold 54, multilayer hollow fiber body 56 according to this invention, integral pleated blood filter 58 received in the gap between the opposite ends of the multilayer hollow fiber body 56, and generally oblong outer housing 60 receiving the barrier 52, manifold 54, body 56 and filter 58. In the apparatus 50, the hollow fibers of the multilayer hollow fiber body 56 extend generally but not precisely parallel with the axis of the heat exchanger barrier 52 and the slot-like exit opening 62 of the inlet manifold 54 so that the blood flow path is almost perpendicular, e.g., 85–89 degrees, to the hollow fibers.

The multilayer hollow fiber body 30 may be formed by manually performing the step of repeatedly folding the mat 20 along the fold lines, FL-1, FL-2, etc., and this manual process has successfully been employed to make prototypes of the body 30. A thin board (not shown) may be used to hold down the previous ply or plies while the next ply is being folded over onto the previous ply.

Most preferably, however, the folding process would be mechanized or automated. For example, the process could be performed using the apparatus 100 illustrated in FIG. 8. The apparatus 100 comprises a plurality of pins 102, 104, 106, 108, 110, 112, 114, 116, 118, 120, 122, 124, 126, 128, 130, 132, 134, 136, 138, etc., slidably received in a plurality of parallel slots 140 in opposite side walls of a frame 141, and a roller 142 for receiving a mat 144 in roll form. It is contemplated that a brake or other mechanism would be operatively connected to the roller 142 to control feeding of the mat 144 into the apparatus 100.

Figure 8:
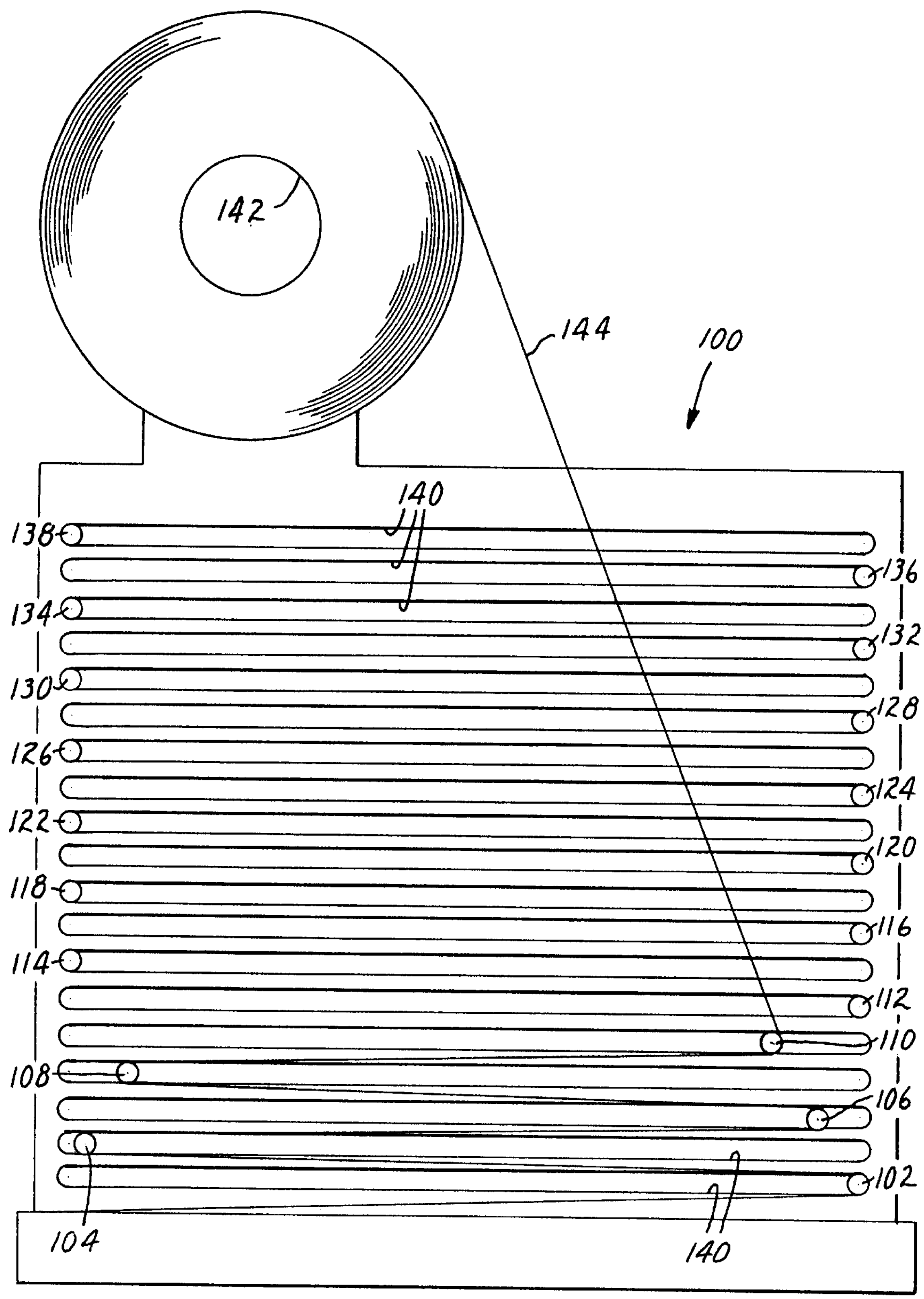
FIG. 8 is schematic vertical cross-sectional view of an apparatus for forming a multilayer hollow fiber body from the elongate mat of FIG. 1.

The pins 102, 104, 106, 108, 110, 112, 114, 116, 118, 120, 122, 124, 126, 128, 130, 132, 134, 136, 138, etc., would initially be positioned at opposite ends of adjacent slots 140 in alternating fashion, and the mat 144 would be feed into the apparatus 100. The free end of the mat 144 would be held, and the pins would successively be brought across their respective slots 140, thus folding the mat 144 across a plurality of fold lines defined by the pins 102, 104, 106, 108, 110, 112, 114, 116, 118, 120, 122, 124, 126, 128, 130, 132, 134, 136, 138, etc. Pins 102, 104, 106, 108 and 110 are shown in FIG. 8 as having their range within their respective slots 140 limited by a control mechanism, such as a computer controlled mechanism, in order to obtain the generally trapezoid-like shape shown in FIG. 4. The pins 102, 104, 106, 108 and 110 could have been allowed to travel the entire distance of their respective slots 140 to form the mat 30D illustrated in FIG. 6. Alternatively, the slots 140 could be provided with successively decreasing length but that would limit the ability to program different configurations for the multilayer bodies produced by the apparatus 100.

Figure 9:
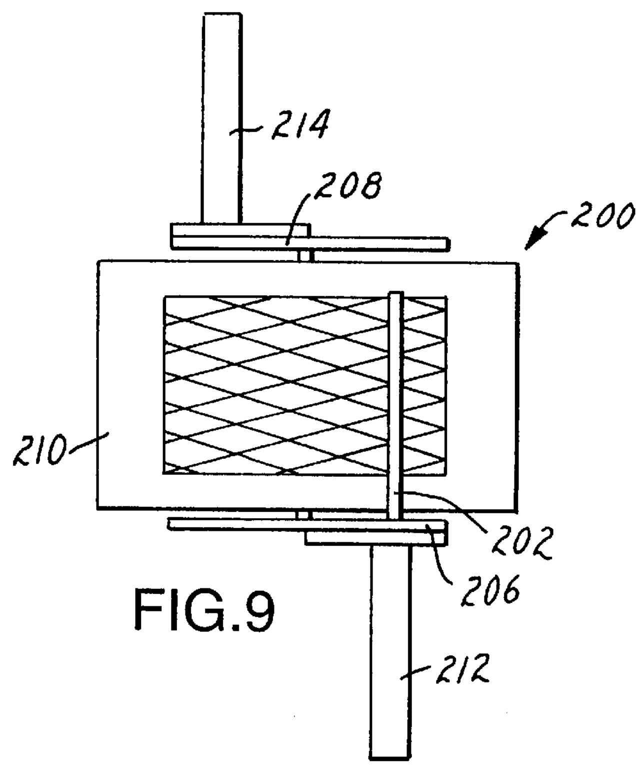
FIG. 9 is top plan view a second embodiment of an apparatus for forming a multilayer hollow fiber body from the elongate mat of FIG. 1.
Figure 10:
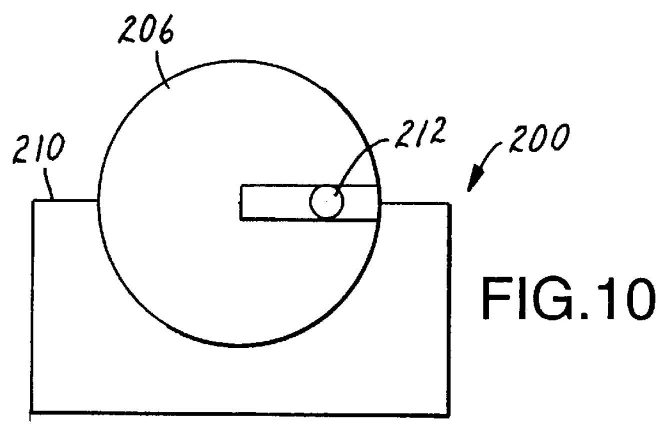
FIG. 10 is a side elevational view of the apparatus of FIG. 9.
Figure 11:
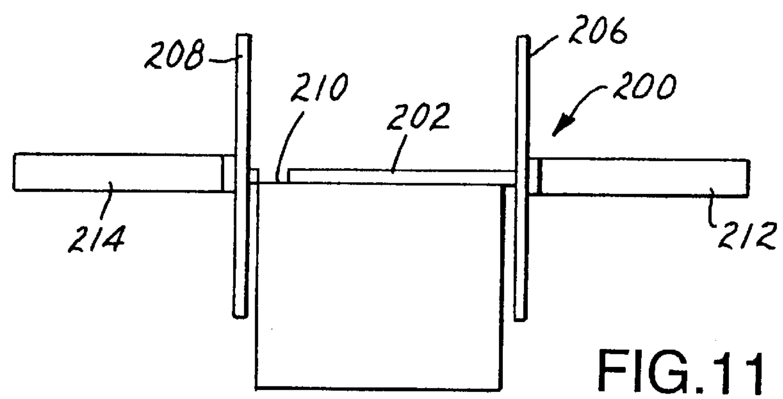
FIG. 11 is a front elevational view of the apparatus of FIGS. 9 and 10.

FIGS. 9–18 illustrate an alternative preferred apparatus 200 and method for producing a multilayer hollow fiber body according to the invention. This apparatus 200 could either be manually operated or computer/machine controlled. The apparatus 200 generally comprises two retractable pins 202 and 204, each mounted on a separate frame rotor 206 and 208, respectively, arranged along opposite sides of a vacuum table 210. Rotor 206 may also be referred to as "rotor A", and rotor 208 may also be referred to as "rotor B" Each rotor 206 and 208 is mounted on the table 210 for rotation relative to the table 210 to pivot the retractable pins 202 and 204 over the surface of the table 210. FIGS. 9–11 illustrate the apparatus 200 as having manually operable handles 212 and 214 mounted on the rotor 206 and 208, respectively, to facilitate manually moving the rotor 206 and 208 and to receive the retracted pins 202 and 204 therein.

Figure 16A:
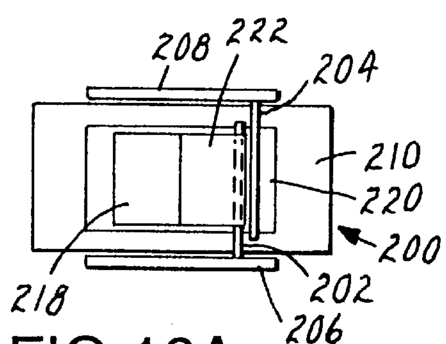
FIGS. 16A and 16B are corresponding top plan and side elevational views of the apparatus of FIGS. 9–15B at a fifth step of folding a mat with the apparatus.
Figure 16B:
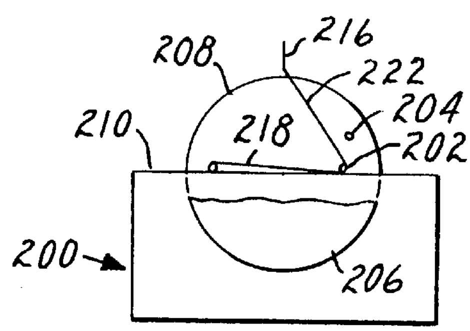
Figure 17A:
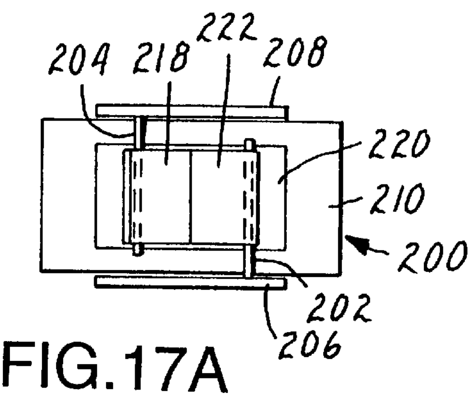
FIGS. 17A and 17B are corresponding top plan and side elevational views of the apparatus of FIGS. 9–16B at a sixth step of folding a mat with the apparatus.
Figure 17B:
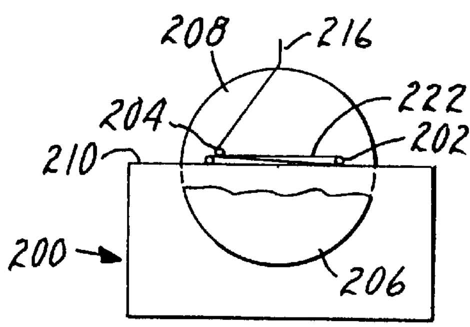
Figure 18:
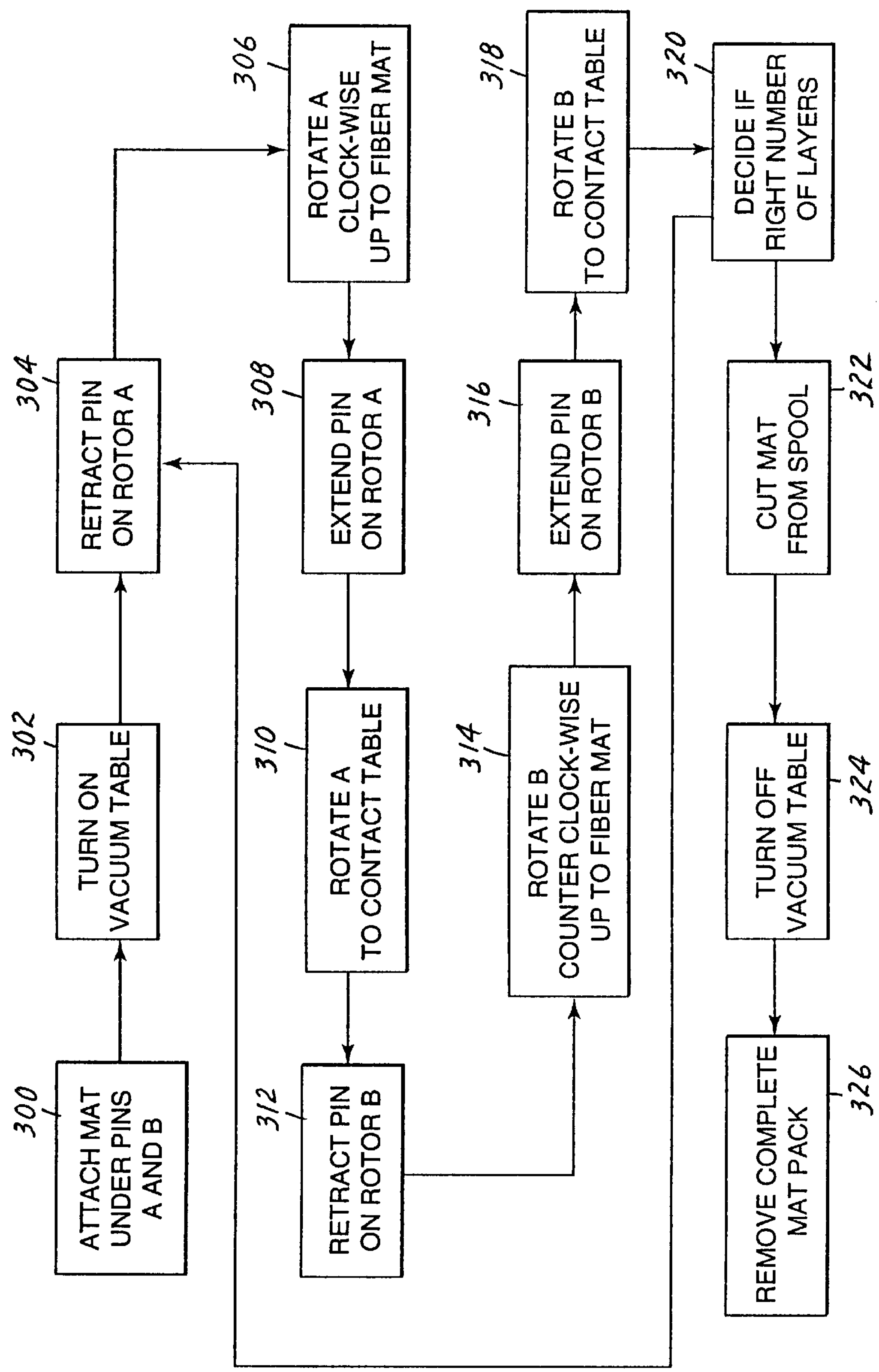
FIG. 18 is a flow diagram of a process of folding a mat with the apparatus of FIGS. 9–17B.

FIGS. 12A–17B and 18 illustrate use of the apparatus 200. In FIGS. 12A–17B, the figures designated with reference characters ending in an "A" show top plan schematic views of the apparatus 200, and the figures designated with reference characters ending in a "B" show side elevational schematic views but otherwise show the apparatus 200 at the same step as the "A" views designated with the same number. FIG. 18 is a flow chart outlining the various process steps used to repeatedly fold the mat, here designated 216, over itself to form the multilayer hollow fiber body.

The mat 216 is first attached to the vacuum table 210 under pins 202 and 204 (step 300), and vacuum is applied to the surface of the table 210 to help retain the mat 216 in position (step 302).

Figure 12A:
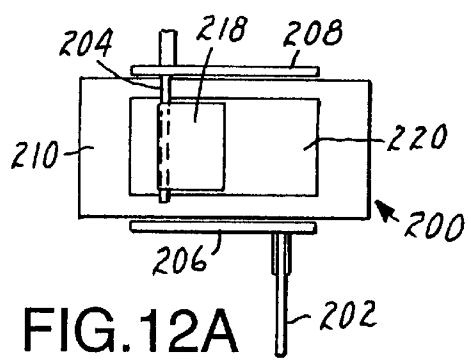
FIGS. 12A and 12B are corresponding top plan and side elevational views of the apparatus of FIGS. 9–11 at a first step of folding a mat with the apparatus.
Figure 12B:
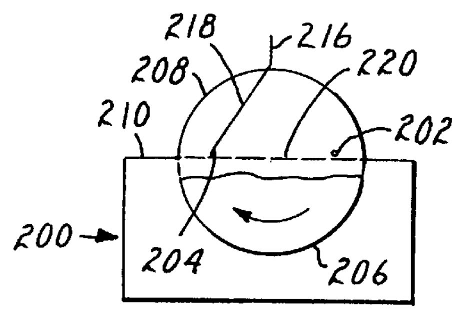
Figure 13A:
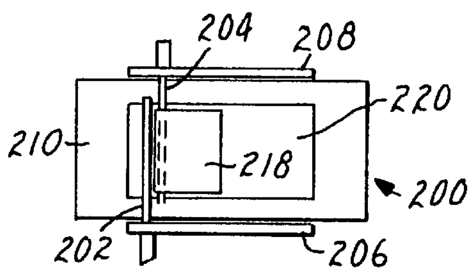
FIGS. 13A and 13B are corresponding top plan and side elevational views of the apparatus of FIGS. 9–12B at a second step of folding a mat with the apparatus.
Figure 13B:
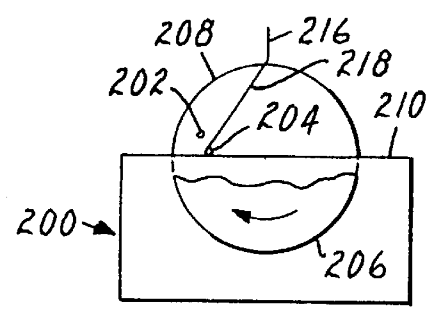
Figure 14A:
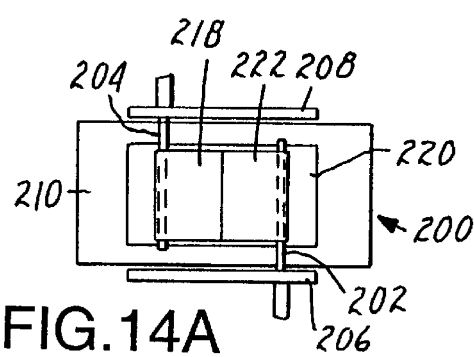
FIGS. 14A and 14B are corresponding top plan and side elevational views of the apparatus of FIGS. 9–13B at a third step of folding a mat with the apparatus.
Figure 14B:
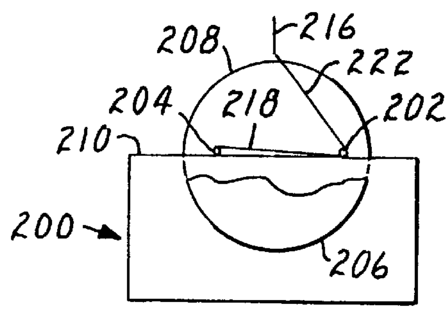

As illustrated in FIGS. 12A and 12B, the mat 216 extends down to the table 210 where it makes a bend as it comes around the second pin 204. The bend around the second pin 204 will constitute a first fold line. As illustrated in FIGS. 12A and 12B and step 304 of FIG. 18, the first pin 202 is moved into its retracted position (step 304), and pin 202 and the "A" rotor 206 are rotated clockwise to position the first pin 202 over to the same side of the table 210 as the second pin 204 is positioned (step 306).

Then, as illustrated in FIGS. 13A–14B, the first pin 202 is moved to its extended position (step 308), and the first pin 202 and "A" rotor 206 are pivoted over the table 210 (step 310), with the first pin 202 engaging the mat 216 above the table 210 and second pin 204 to bring another ply 218 across the table 210 over the ply 220 held by the second pin 204. In step 310, the second pin 204 remains stationary holding the previously formed ply 220 in position over the table 210. The mat 216 now makes a bend around the first pin 202 adjacent the surface of the table 210. This bend around the first pin 202 will constitute a second fold line.

Since the first and second pins 202 and 204 are parallel to one another, the first and second fold lines will also be parallel to one another. The first and second pins 202 and 204 are also perpendicular to the longitudinal direction of the mat 216 to further define the fold lines as being perpendicular to the longitudinal direction of the mat 216.

Figure 15A:
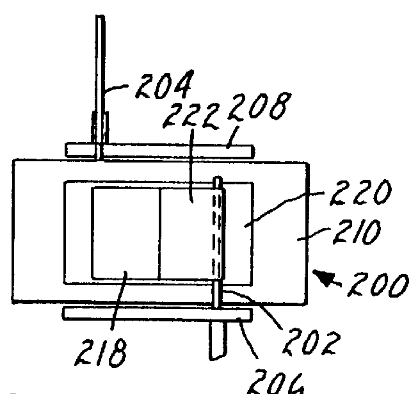
FIGS. 15A and 15B are corresponding top plan and side elevational views of the apparatus of FIGS. 9–14B at a fourth step of folding a mat with the apparatus.
Figure 15B:
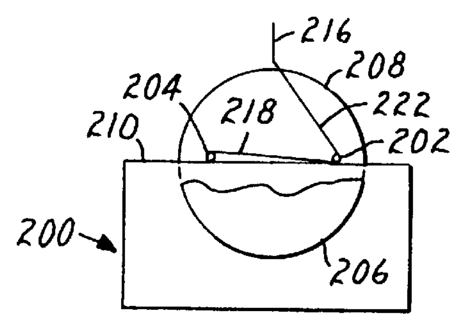

Next, as illustrated in FIGS. 15A–B, the second pin 204 is retracted in step 312, and the "B" rotor 208 and second pin 204 are pivoted counterclockwise in step 314 to position the second pin 204 over to the same side of the table 210 as the first pin 202 is positioned. Then, the second pin 204 is moved to its extended position (step 316; FIGS. 16A–B), and the second pin 204 and "B" rotor 208 are pivoted over the table 210 (step 318;

FIGS. 17A–B), with the second pin 204 engaging the mat 216 above the table 210 and first pin 202 to bring another ply 222 across the table 210 over the ply 218 held by the first pin 202. In step 318, the first pin 202 remains stationary holding the previously formed ply 218 in position over the table 210 and previous plies, e.g., ply 220. The mat 216 now makes a bend around the second pin 204 adjacent the surface of the table 210. This bend around the first pin 204 will constitute a third fold line.

Step 320 is a decision step in which a decision must be made as to whether a sufficient number of plies have been formed. Until a sufficient number of plies have been formed, the process returns to step 304 and repeats steps 304–320. After a sufficient number of plies have been formed, the mat 216 is cut from the spool (not shown) to separate the multilayer hollow fiber body from the roll-form stock of mat material (step 322). Vacuum to the vacuum table 210 is turned off in step 324, and the completed multilayer hollow fiber body is removed from the apparatus 300 in step 326 so that it may be assembled in the desired product, e.g., a blood oxygenator.

The opposite lateral sides of the hollow fiber body may be embedded in potting compound as is conventional in the art of forming membrane blood oxygenators.

The oblique angle σ of the hollow fibers 22 relative to the fold lines FL-1, FL-2, . . ., FL-N is preferably sufficiently great to prevent nesting of the hollow fibers 22 of one ply between the hollow fibers 22 of either adjacent ply. The specified range of oblique angle σ of 1–15 degrees (most preferably 5 degrees) is believed to accomplish this result.

The multilayer hollow fiber body of this invention may be employed in various devices, particularly including integral blood oxygenator, heat exchanger and filter units, as well as other devices. Because the body is not formed by continuously wrapping a multiplicity of layers over a core, it is particularly suitable for uses where it is desirable to have a gap between the ends of the body or in which it is desirable to retain the body in a generally flat configuration. The multilayer hollow fiber body of this invention provides this flexibility in the design of the devices into which it is employed.

One advantage of this feature, is that a blood filter 58 (FIG. 19) may be employed immediately downstream of the hollow fiber body 56 and blood may pass directly from the hollow fiber body 56 to the filter 58 without intervening collection or distribution manifolds. The blood exits the hollow fiber body 56 in appropriate distributed pattern to pass directly into the filter 58.

An additional advantage is that this hollow fiber body may be formed from a single mat. There is no need to combine two separate mats into one structure in order to obtain the proper orientation of the hollow fibers of adjacent layers of the hollow fiber body. There is no need to wind a single hollow fiber over a core in a complicated operation.

As various changes could be made in the above constructions and methods without departing from the scope of the invention as defined in the claims, it is intended that all matter contained in the above description or shown in the accompanying drawings be interpreted as illustrative and not in a limiting sense.

I claim:

1. A multilayer hollow fiber body comprising a single hollow fiber mat arranged in the form of a body comprising a plurality of hollow fiber plies;

the mat comprising a plurality of hollow fibers a plurality of connecting fibers, the hollow fibers being held by the connecting fibers; and the mat being repeatedly folded over on itself along fold lines, each of which is at an oblique angle to the hollow fibers, to form a multilayer hollow fiber body in which the hollow fibers of any ply of the multilayer hollow fiber body are disposed so as to cross the hollow fibers of an adjacent successive ply of the multilayer hollow fiber body.

2. A multilayer hollow fiber body according to claim 1 wherein the fold lines are generally parallel to one another.

3. A multilayer hollow fiber body according to claim 1 wherein the oblique angle between the hollow fibers and the fold lines is between approximately 1–15 degrees.

4. A multilayer hollow fiber body according to claim 3 wherein the mat is elongate, the hollow fibers extend at an oblique angle with respect to the direction of elongation of the mat, the fold lines being generally perpendicular to the direction of elongation of the mat.

5. A multilayer hollow fiber body according to claim 4 wherein the connecting fibers are disposed at regular intervals and extend generally in the direction of elongation of the mat, the connecting fibers being interweaved with the hollow fibers to hold the fibers in the mat.

6. A multilayer hollow fiber body according to claim 5 wherein the connecting fibers are:

substantially solid disposed at generally regular intervals; and extend generally in the longitudinal direction of the mat.

7. A multilayer hollow fiber body according to claim 6 wherein the hollow fibers each comprise a lumen and a wall defining the lumen, the wall being porous allowing transfer of gas but not liquid through the wall of the hollow fiber.

8. A multilayer hollow fiber body according to claim 7 wherein the body is formed in a generally arcuate configuration over a manifold.

9. A multilayer hollow fiber body according to claim 8 wherein the ply adjacent the manifold constitutes an inner ply and the ply farthest from the manifold constitutes an outer ply, the distance between fold lines along a ply being greater the closer that ply is to the outer ply.

10. A multilayer hollow fiber body according to claim 7 wherein the distance between the fold lines along any ply is the same as the distance between the fold lines along any other ply.

11. A method of making a multilayer hollow fiber body comprising the following steps:

interweaving hollow fibers and connecting fibers to form a mat, with the hollow fibers being generally parallel to one another; and repeatedly folding the mat over on itself along fold lines that are at an oblique angle to the hollow fibers to form a multilayer hollow fiber body in which the hollow fibers of any ply of the multilayer hollow fiber body are disposed so as to cross the hollow fibers of an adjacent successive ply of the multilayer hollow fiber body.

12. A method according to claim 11 wherein the step of repeatedly folding the mat over on itself further comprises folding the mat along generally parallel fold lines that are generally perpendicular to the direction of elongation of the mat.

13. A method according to claim 12 where the step of folding the mat along generally parallel fold lines that are generally perpendicular to the direction of elongation of the mat comprises folding the mat along generally parallel fold lines that are generally perpendicular to the direction of elongation of the mat and that are equally spaced apart so that any ply of the mat has a length between fold lines that is generally equal to the length of the other plies.

* * * * *